United States Patent
Adams et al.

(10) Patent No.: US 6,949,122 B2
(45) Date of Patent: Sep. 27, 2005

(54) FOCUSED COMPRESSION MITRAL VALVE DEVICE AND METHOD

(75) Inventors: John M. Adams, Sammamish, WA (US); David G. Reuter, Bothell, WA (US); Mark L. Mathis, Kirkland, WA (US); Scott J. Wolf, Bellevue, WA (US)

(73) Assignee: Cardiac Dimensions, Inc., Kirkland, WA (US)

( * ) Notice: Subject to any disclaimer, the term of this patent is extended or adjusted under 35 U.S.C. 154(b) by 345 days.

(21) Appl. No.: 10/003,910

(22) Filed: Nov. 1, 2001

(65) Prior Publication Data

US 2003/0083538 A1 May 1, 2003

(51) Int. Cl.⁷ .................................................. A61F 2/24
(52) U.S. Cl. ....................................... 623/2.36; 623/2.11
(58) Field of Search .................... 600/16–18; 623/1.15, 623/1.11, 1.16, 1.18, 1.22, 2.1–2.42

(56) References Cited

U.S. PATENT DOCUMENTS

| | | |
|---|---|---|
| 4,055,861 A | 11/1977 | Carpentier et al. |
| 4,164,046 A | 8/1979 | Cooley |
| 4,485,816 A | 12/1984 | Krumme |
| 4,550,870 A | 11/1985 | Krumme et al. |
| 4,830,023 A | 5/1989 | de Toledo et al. |
| 5,061,277 A | 10/1991 | Carpentier et al. |
| 5,250,071 A | 10/1993 | Palermo |
| 5,261,916 A | 11/1993 | Engelson |
| 5,265,601 A | 11/1993 | Mehra |
| 5,350,420 A | 9/1994 | Cosgrove et al. |
| 5,514,161 A | 5/1996 | Limousin |
| 5,554,177 A | 9/1996 | Kieval et al. |
| 5,562,698 A | 10/1996 | Parker |
| 5,584,867 A | 12/1996 | Limousin et al. |
| 5,601,600 A | 2/1997 | Ton |
| 5,733,325 A | 3/1998 | Robinson et al. |
| 5,824,071 A | 10/1998 | Nelson et al. |
| 5,891,193 A | 4/1999 | Robinson et al. |
| 5,895,391 A | 4/1999 | Farnholtz |
| 5,908,404 A | 6/1999 | Elliott |
| 5,935,161 A | 8/1999 | Robinson et al. |
| 5,961,545 A | 10/1999 | Lentz et al. |
| 5,984,944 A | 11/1999 | Forber |

(Continued)

FOREIGN PATENT DOCUMENTS

| | | |
|---|---|---|
| WO | WO 00/44313 A1 | 8/2000 |
| WO | WO 00/60995 A3 | 10/2000 |
| WO | WO 01/00111 A1 | 1/2001 |
| WO | WO 01/50985 A1 | 7/2001 |
| WO | WO 01/54618 | 8/2001 |
| WO | WO 01/87180 A2 | 11/2001 |
| WO | WO 02/00099 A2 | 1/2002 |
| WO | WO 02/01999 A2 | 1/2002 |
| WO | WO 02/05888 A1 | 1/2002 |
| WO | WO 02/19951 A1 | 3/2002 |
| WO | WO 02/34118 A2 | 5/2002 |
| WO | WO 02/47539 A2 | 6/2002 |
| WO | WO 02/62263 A2 | 8/2002 |
| WO | WO 02/62270 A1 | 8/2002 |
| WO | WO 02/62408 A2 | 8/2002 |
| WO | WO 02/76284 A2 | 10/2002 |
| WO | WO 02/78576 A2 | 10/2002 |
| WO | WO 02/96275 A2 | 12/2002 |
| WO | WO 03/49647 A1 | 6/2003 |

*Primary Examiner*—Scott M. Getzow
(74) *Attorney, Agent, or Firm*—Wilson Sonsini Goodrich & Rosati (57) ABSTRACT

A mitral valve therapy device and method treats dilated cardiomyopathy. The device is configured to be placed in the coronary sinus of a heart adjacent to the mitral valve annulus. The device includes a force distributor that distributes an applied force along a pericardial wall of the coronary sinus, and a force applier that applies the applied force to one or more discrete portions of a wall of the coronary sinus adjacent to the mitral valve annulus to reshape the mitral valve annulus in a localized manner.

65 Claims, 5 Drawing Sheets

U.S. PATENT DOCUMENTS

| | | | |
|---|---|---|---|
| 6,027,517 A | 2/2000 | Crocker et al. |
| 6,077,295 A | 6/2000 | Limon et al. |
| 6,077,297 A | 6/2000 | Robinson et al. |
| 6,099,549 A | 8/2000 | Bosma et al. |
| 6,099,552 A | 8/2000 | Adams |
| 6,129,755 A | 10/2000 | Mathis et al. |
| 6,190,406 B1 | 2/2001 | Duerig et al. |
| 6,210,432 B1 | 4/2001 | Solem et al. |
| 6,275,730 B1 | 8/2001 | KenKnight et al. |
| 6,342,067 B1 | 1/2002 | Mathis et al. |
| 6,352,553 B1 | 3/2002 | van der Burg et al. |
| 6,352,561 B1 | 3/2002 | Leopold et al. |
| 6,395,017 B1 | 5/2002 | Dwyer et al. |
| 6,402,781 B1 | 6/2002 | Langberg et al. |
| 6,419,696 B1 | 7/2002 | Ortiz et al. |
| 6,442,427 B1 | 8/2002 | Boute et al. |
| 6,503,271 B2 | 1/2003 | Duerig et al. |
| 6,537,314 B2 | 3/2003 | Langberg et al. |
| 6,569,198 B1 | 5/2003 | Wilson et al. |
| 6,589,208 B2 | 7/2003 | Ewers et al. |
| 6,602,288 B1 | 8/2003 | Cosgrove et al. |
| 6,602,289 B1 | 8/2003 | Colvin et al. |
| 6,623,521 B2 | 9/2003 | Steinke et al. |
| 6,626,899 B2 | 9/2003 | Houser et al. |
| 2001/0018611 A1 | 8/2001 | Solem et al. |
| 2001/0044568 A1 | 11/2001 | Langberg et al. |
| 2001/0049558 A1 | 12/2001 | Liddicoat et al. |
| 2002/0016628 A1 | 2/2002 | Langberg et al. |
| 2002/0035361 A1 | 3/2002 | Houser et al. |
| 2002/0042621 A1 | 4/2002 | Liddicoat et al. |
| 2002/0042651 A1 | 4/2002 | Liddicoat et al. |
| 2002/0049468 A1 | 4/2002 | Streeter et al. |
| 2002/0055774 A1 | 5/2002 | Liddicoat |
| 2002/0065554 A1 | 5/2002 | Streeter |
| 2002/0087173 A1 | 7/2002 | Alferness et al. |
| 2002/0095167 A1 | 7/2002 | Liddicoat et al. |
| 2002/0103532 A1 | 8/2002 | Langberg et al. |
| 2002/0103533 A1 | 8/2002 | Langberg et al. |
| 2002/0138044 A1 | 9/2002 | Streeter et al. |
| 2002/0151961 A1 | 10/2002 | Lashinski et al. |
| 2002/0169502 A1 | 11/2002 | Mathis |
| 2002/0169504 A1 | 11/2002 | Alferness et al. |
| 2002/0183835 A1 | 12/2002 | Taylor et al. |
| 2002/0183836 A1 | 12/2002 | Liddicoat et al. |
| 2002/0183837 A1 | 12/2002 | Streeter et al. |
| 2002/0183838 A1 | 12/2002 | Liddicoat et al. |
| 2002/0183841 A1 | 12/2002 | Cohn et al. |
| 2003/0018358 A1 | 1/2003 | Saadat |
| 2003/0069636 A1 | 4/2003 | Solem et al. |
| 2003/0078465 A1 | 4/2003 | Pai et al. |
| 2003/0078654 A1 | 4/2003 | Taylor et al. |
| 2003/0083538 A1 | 5/2003 | Adams et al. |
| 2003/0105520 A1 | 6/2003 | Alferness et al. |
| 2003/0130731 A1 | 7/2003 | Vidlund et al. |
| 2003/0135267 A1 | 7/2003 | Solem et al. |
| 2003/0144697 A1 | 7/2003 | Mathis et al. |
| 2003/0171776 A1 | 9/2003 | Adams et al. |
| 2003/0171806 A1 | 9/2003 | Mathis et al. |
| 2003/0212453 A1 | 11/2003 | Mathis et al. |

FOCUSED COMPRESSION MITRAL VALVE DEVICE AND METHOD

FIELD OF THE INVENTION

The present invention generally relates to a device and method for treating dilated cardiomyopathy of a heart. The present invention more particularly relates to a device and method for delivering a localized force to the mitral valve annulus to reshape the mitral valve annulus.

BACKGROUND OF THE INVENTION

The human heart generally includes four valves. Of these valves, a most critical one is known as the mitral valve. The mitral valve is located in the left atrial ventricular opening between the left atrium and left ventricle. The mitral valve is intended to prevent regurgitation of blood from the left ventricle into the left atrium when the left ventricle contracts. In preventing blood regurgitation the mitral valve must be able to withstand considerable back pressure as the left ventricle contracts.

The valve cusps of the mitral valve are anchored to muscular wall of the heart by delicate but strong fibrous cords in order to support the cusps during left ventricular contraction. In a healthy mitral valve, the geometry of the mitral valve ensures that the cusps overlie each other to preclude regurgitation of the blood during left ventricular contraction.

The normal functioning of the mitral valve in preventing regurgitation can be impaired by dilated cardiomyopathy caused by disease or certain natural defects. For example, certain diseases may cause dilation of the mitral valve annulus. This can result in deformation of the mitral valve geometry to cause ineffective closure of the mitral valve during left ventricular contraction. Such ineffective closure results in leakage through the mitral valve and regurgitation. Diseases such as bacterial inflammations of the heart or heart failure can cause the aforementioned distortion or dilation of the mitral valve annulus. Needless to say, mitral valve regurgitation must not go uncorrected.

One method of repairing a mitral valve having impaired function is to completely replace the valve. This method has been found to be particularly suitable for replacing a mitral valve when one of the cusps has been severely damaged or deformed. While the replacement of the entire valve eliminates the immediate problem associated with a dilated mitral valve annulus, presently available prosthetic heart valves do not possess the same durability as natural heart valves.

Various other surgical procedures have been developed to correct the deformation of the mitral valve annulus and thus retain the intact natural heart valve function. These surgical techniques involve repairing the shape of the dilated or deformed valve annulus. Such techniques, generally known as annuloplasty, require surgically restricting the valve annulus to minimize dilation. Here, a prosthesis is typically sutured about the base of the valve leaflets to reshape the valve annulus and restrict the movement of the valve annulus during the opening and closing of the mitral valve.

Many different types of prostheses have been developed for use in such surgery. In general, prostheses are annular or partially annular shaped members which fit about the base of the valve annulus. The annular or partially annular shaped members may be formed from a rigid material, such as a metal, or from a flexible material.

While the prior art methods mentioned above have been able to achieve some success in treating mitral regurgitation, they have not been without problems and potential adverse consequences. For example, these procedures require open heart surgery. Such procedures are expensive, are extremely invasive requiring considerable recovery time, and pose the concomitant mortality risks associated with such procedures. Moreover, such open heart procedures are particularly stressful on patients with a comprised cardiac condition. Given these factors, such procedures are often reserved as a last resort and hence are employed late in the mitral regurgitation progression. Further, the effectiveness of such procedures is difficult to assess during the procedure and may not be known until a much later time. Hence, the ability to make adjustments to or changes in the prostheses to obtain optimum effectiveness is extremely limited. Later corrections, if made at all, require still another open heart surgery.

An improved therapy to treat mitral regurgitation without resorting to open heart surgery has recently been proposed. This is rendered possible by the realization that the coronary sinus of a heart is near to and at least partially encircles the mitral valve annulus and then extends into a venous system including the great cardiac vein. As used herein, the term "coronary sinus" is meant to refer to not only the coronary sinus itself but in addition, the venous system associated with the coronary sinus including the great cardiac vein. The therapy contemplates the use of a device introduced into the coronary sinus to reshape and advantageously effect the geometry of the mitral valve annulus.

The device includes a resilient member having a cross sectional dimension for being received within the coronary sinus of the heart and a longitudinal dimension having an unstressed arched configuration when placed in the coronary sinus. The device partially encircles and exerts an inward pressure on the mitral valve. The inward pressure constricts the mitral valve annulus, or at least a portion of it, to essentially restore the mitral valve geometry. This promotes effective valve sealing action and eliminates mitral regurgitation.

The device may be implanted in the coronary sinus using only percutaneous techniques similar to the techniques used to implant cardiac leads such as pacemaker leads. One proposed system for implanting the device includes an elongated introducer configured for being releasably coupled to the device. The introducer is preferably flexible to permit it to advance the device into the heart and into the coronary sinus through the coronary sinus ostium. To promote guidance, an elongated sheath is first advanced into the coronary sinus. Then, the device and introducer are moved through a lumen of the sheath until the device is in position within the coronary sinus. Because the device is formed of resilient material, it conforms to the curvatures of the lumen as it is advanced through the sheath. The sheath is then partially retracted to permit the device to assume its unstressed arched configuration. Once the device is properly positioned, the introducer is then decoupled from the device and retracted through the sheath. The procedure is then completed by the retraction of the sheath. As a result, the device is left within the coronary sinus to exert the inward pressure on the mitral valve to restore mitral valve geometry.

The foregoing therapy has many advantages over the traditional open heart surgery approach. Since the device, system and method may be employed in a comparatively noninvasive procedure, mitral valve regurgitation may be treated at an early stage in the mitral regurgitation progression. Further, the device may be placed with relative ease by any minimally invasive cardiologist. Still further, since the heart remains completely intact throughout the procedure, the effectiveness of the procedure may be readily determined. Moreover, should adjustments be deemed desirable, such adjustments may be made during the procedure and before the patient is sent to recovery.

Unfortunately, the human anatomy does impose some obstacles to this recently proposed procedure for treating mitral regurgitation. More specifically, the human heart includes a coronary artery which descends from the aorta. One branch of the coronary artery is the circumflex artery which, in turn, includes the left marginal branch of the circumflex artery. As used herein, the term "circumflex artery" is taken to include the circumflex artery itself or any branch therefrom. The circumflex artery extends distally generally along the coronary sinus but at a point proximal to the coronary artery, it passes under the coronary sinus. The circumflex artery supports blood flow important to the viability of the heart. Hence, reduction in this blood flow must be avoided. As a result, a device placed in the coronary sinus must not be permitted to extend within the coronary sinus beyond the crossover point of the circumflex artery and the coronary sinus in a way which impedes blood flow in the circumflex artery.

While the foregoing therapy provides many benefits over previous therapies, the therapy still contemplates the general reshaping of the mitral valve annulus. To that end, the devices encircle more than half of the mitral valve annulus in an attempt to provide generalized mitral valve annulus reshaping. While this indeed may be successful, it may be unnecessary.

Recently, it has been observed that the application of a localized force against a discrete portion of the mitral valve annulus can terminate mitral regurgitation. This suggests that mitral valve dilation may be localized and nonuniform. Hence, while devices that attempt to encircle the mitral valve as much as possible for providing generalized reshaping of the mitral valve annulus may be effective in treating mitral regurgitation, a localized reshaping therapy may only be needed. Such localized therapy would have all the benefits of the generalized therapy. In addition, a localized therapy device may be easier to implant and adjust. Further, a localized therapy device may not require the length of a generalized therapy device, thus providing the additional advantage of eliminating the need of avoiding the circumflex artery all together.

SUMMARY OF THE INVENTION

The invention provides a mitral valve therapy device configured to be placed in the coronary sinus of a heart adjacent to the mitral valve annulus. The device includes a force applier that applies an applied force to a discrete portion of the atrial wall of the coronary sinus adjacent to the mitral valve annulus to concentrate the applied force on a discrete portion of the mitral valve annulus.

The force applier preferably has a cross-sectional dimension greater than the unstressed cross-sectional dimension of the coronary sinus to change the shape of the mitral valve annulus. The force applier also preferably has an axial length substantially less than half the circumference of the mitral valve annulus.

The device may be an expandable structure that expands from a collapsed condition to an expanded condition defining a deployed transverse dimension greater than the unstressed diameter of the coronary sinus. The device may be a frame structure. The device may be balloon expandable, mechanically expandable, or self-expandable.

The device may further include a force distributor that distributes the applied force along a pericardial wall of the coronary sinus. The force applier may be configured to apply the applied force to a plurality of discrete portions of the atrial wall of the coronary sinus. The surface area of the force distributor is preferably substantially greater than the surface area of the force applier.

The present invention further provides a mitral valve therapy device configured to be placed in the coronary sinus of a heart adjacent to the mitral valve annulus, the device including a force distributor and a force applier. The force distributor distributes an applied force along a pericardial wall of the coronary sinus and the force applier applies the applied force to at least one discrete portion of a wall of the coronary sinus adjacent to the mitral valve annulus to concentrate the applied force on at least one discrete portion of the mitral valve annulus.

The force applier has a length substantially less than one half the mitral valve annulus circumference. The force applier may apply the applied force to a plurality of discrete portions of the wall of the coronary sinus adjacent to the mitral valve annulus.

The force distributor may include an elongated first member configured to substantially continuously contact the pericardial wall of the coronary sinus and the force applier may include a second member extending from the first member at an angle and having an end that applies the applied force.

The second member may be resiliently connected to the first member. The first and second members may be integrally formed from a same elongated member which may be formed from a resilient material. The second member extend from the first member intermediate opposed ends of the first member.

The force applier may further include at least one additional member extending from the first member intermediate the opposed ends of the first member. The at least one additional member may extend from the first member substantially parallel to the second member. The first and second members may form an integral structure.

The force distributor may be an elongated frame structure and the force applier may be at least one columnar frame structure extending from the elongated frame structure. The at least one columnar frame structure is preferably expandable from a collapsed condition to an expanded columnar condition. The at least one columnar frame structure may be balloon expandable or self-expandable.

The elongated frame structure may also be expandable from a collapsed condition to an expanded condition. The elongated frame structure may be balloon expandable or self-expandable.

The force applier may include a plurality of columnar frame structures. The plurality of columnar frame structures preferably are expandable from a collapsed condition to an expanded columnar condition. The plurality of columnar frame structures may be balloon expandable or self-expandable.

The device may be an elongated frame structure. The elongated frame structure may have a portion of increased transverse dimension to form the force applier. The elongated frame structure may be expandable in transverse dimension and be balloon expandable.

The device may be an elongated member having outwardly curved end portions that engage the pericardial wall of the coronary sinus to form the force distributor and an inwardly curved portion between the outwardly curved end portions to form the force applier.

The invention further provides a method of treating dilated cardiomyopathy of a heart including the step of applying a force to a discrete localized portion of an atrial wall of a coronary sinus to concentrate the force on a corresponding localized portion of a mitral valve annulus to change the shape of the mitral valve annulus. The applying step may include the step of implanting a force applying device in the coronary sinus, the device applying the force to the discrete localized portion of the coronary sinus. The device is preferably expandable from a collapsed condition to a deployed condition. The implanting step is preferably carried out while the device is in the collapsed condition, and the device is preferably expanded to the deployed condition after the device is implanted. The device may be self-expandable, expanded with a balloon, or be mechanically expandable.

The method may further include the step of distributing the applied force along a pericardial wall of the coronary sinus. The applying step may include the step of applying the force to a plurality of discrete localized portions of the atrial wall of the coronary sinus while the applied force is distributed along the pericardial wall of the coronary sinus. The applying step may include the step of implanting a force applying device in the coronary sinus, the device applying the force to the plurality of discrete localized portions of the coronary sinus. The device is preferably expandable from a collapsed condition to a deployed condition and the implanting step is preferably carried out while the device is in the collapsed condition. The device may then be expanded to the deployed condition after the device is implanted.

BRIEF DESCRIPTION OF THE DRAWINGS

The features of the present invention which are believed to be novel are set forth with particularity in the appended claims. The invention, together with further aspects and advantages thereof, may best be understood by making reference to the following description taken in conjunction with the accompanying drawings, and the several figures of which like reference numerals identify identical elements, and wherein:

DETAILED DESCRIPTION OF THE INVENTION

Figure 1:
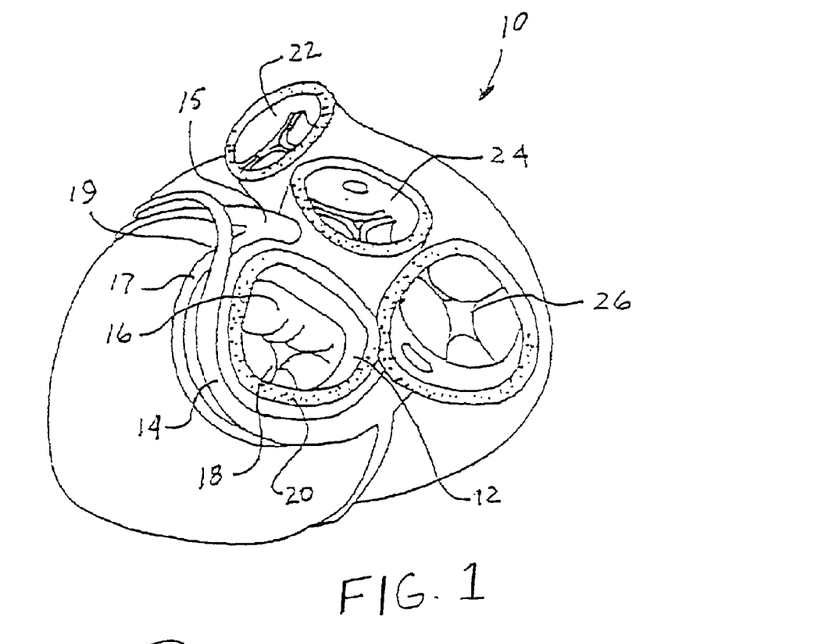
FIG. 1 is a superior view of a human heart with the atria removed.

Referring now to FIG. 1, it is a superior view of a human heart 10 with the atria removed to expose the mitral valve 12, the coronary sinus 14, the coronary artery 15, and the circumflex artery 17 of the heart 10 to lend a better understanding of the present invention. Also generally shown in FIG. 1 are the pulmonary valve 22, the aortic valve 24, and the tricuspid valve 26 of the heart 10.

The mitral valve 12 includes an anterior cusp 16, a posterior cusp 18 and an annulus 20. The annulus encircles the cusps 16 and 18 and maintains their spacing to provide a complete closure during a left ventricular contraction. As is well known, the coronary sinus 14 partially encircles the mitral valve 12 adjacent to the mitral valve annulus 20. As is also known, the coronary sinus is part of the venus system of the heart and extends along the AV groove between the left atrium and the left ventricle. This places the coronary sinus essentially within the same plane as the mitral valve annulus making the coronary sinus available for placement of the mitral valve therapy device of the present invention therein.

The circumflex artery 17 branches from the coronary artery 15 and supplies blood flow to critical tissue of the heart 10. The circumflex artery passes beneath the coronary sinus 14 at a crossover point 19. As will be seen hereinafter, the devices of the present invention avoid constriction of blood flow through the circumflex artery 17 when deployed in the coronary sinus 14.

Figure 2:
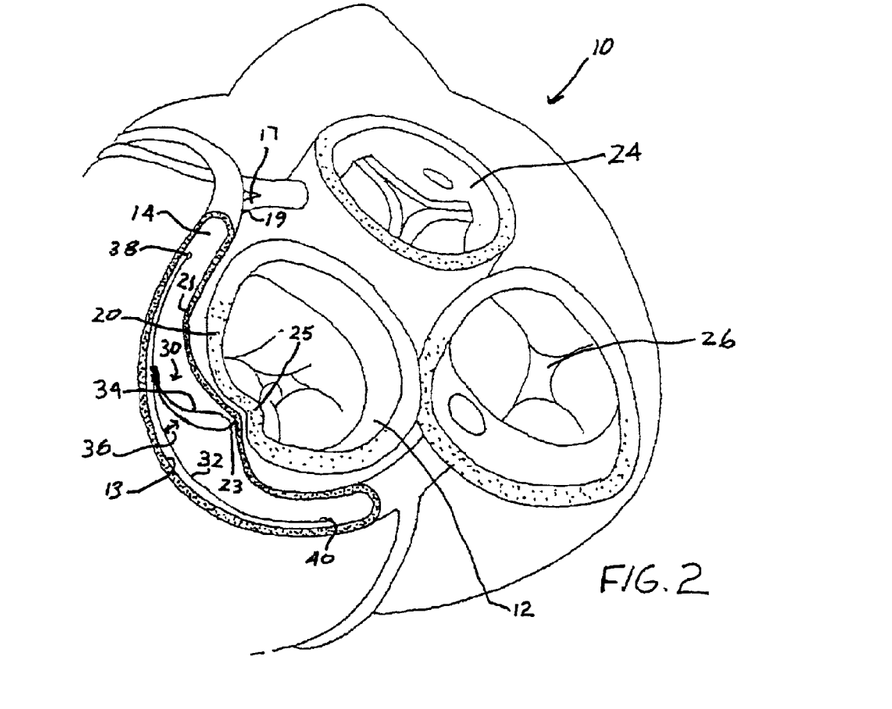
FIG. 2 is a superior view of a human heart similar to FIG. 1 illustrating a deployed mitral valve device embodying the present invention.

FIG. 2 shows a mitral valve therapy device 30 embodying the present invention. As may be noted in FIG. 2, the device 30 has an elongated base or first member 32 having an arched configuration to substantially continuously contact the pericardial wall 13 of the coronary sinus 14. As will be seen hereinafter, the base 32 forms an applied force distributor that distributes a force applied to the atrial wall 21 of the coronary sinus 14 and the adjacent mitral valve annulus 20 that reshapes the mitral valve annulus for terminating mitral regurgitation. To that end, the device includes a second member 34 which extends from the first member 32 at an angle 36. The second member 34 extends from the base 32 intermediate the ends 38 and 40 of the base. The second member contacts the atrial wall 21 of the coronary sinus 14 to apply an applied force to a localized discrete portion 23 thereof and a corresponding localized discrete portion 25 of the mitral valve annulus 20. Hence, the applied force as illustrated, reshapes the mitral valve annulus 20.

The force applying second member 34 may take a configuration of a loop as shown or other configuration providing an end 42 which will apply the applied force without piercing or otherwise damaging the coronary sinus 14 or mitral valve annulus. The device 32 is preferably formed of a resilient biocompatible material. To that end, the device 32 may be formed of, for example, Nitinol, a nickel titanium alloy, well known in the art. This material, as is well known, is capable of being preformed but manipulated to be straight or partially bent while having sufficient memory to return to its preformed configuration. Stainless steel is also among the materials which may be used in forming the device 30. The first and second members 32 and 34 may be formed of the same material as an integral structure or may be formed of different materials.

As will be noted in FIG. 2, the distal end 38 of the base 32 terminates proximally of the crossover point 19 of the circumflex artery 17 and coronary sinus 14. Hence, the device 32 avoids adversely effecting the blood supply provided by the circumflex artery.

Figure 3:
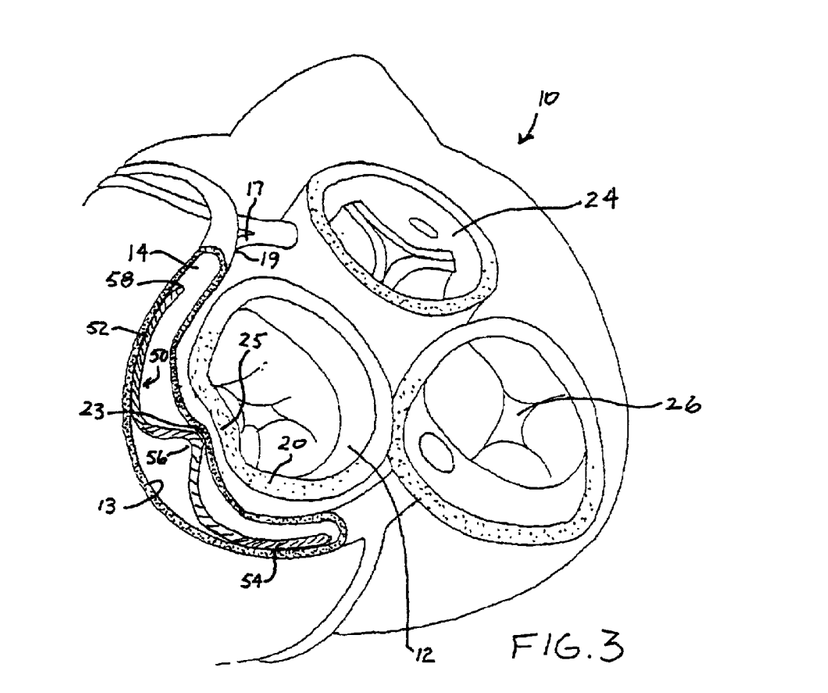
FIG. 3 is a superior view of a human heart similar to FIG. 1 illustrating another deployed mitral valve device embodying the present invention.

Referring now to FIG. 3, it illustrates another mitral valve device 50 embodying the present invention implanted in the coronary sinus 14 of the heart 10. The device 50 is formed from a single elongated member of material which may be any one of the materials previously referred to. The device 50 includes a pair of outwardly curved end portions 52 and 54 that substantially continuously engage the pericardial wall 13 of the coronary sinus 14. The end portions 52 and 54 thus form the force distributor of the device 50 that distributes an applied force along the pericardial wall 13 of the coronary sinus 14. The device 50 further includes an inwardly curved portion 56 between the outwardly curved end portions 52 and 54 to form the force applier. As will be noted in FIG. 3, the force applier 56 applies an applied force to a localized discrete portion 23 of the atrial wall 21 of the coronary sinus 14. This in turn applies the applied force to the corresponding localized discrete portion 25 of the mitral valve annulus 20. The foregoing results in the reshaping of the mitral valve annulus 20 for treating dilated cardiomyopathy.

It may also be noted in FIG. 3 that the distal end 58 of the device 50 is proximal to the crossover point 19 of the circumflex artery 17 and the coronary sinus 14. Hence, in accordance with this embodiment, the blood supply of the circumflex artery is not effected by the device 50.

Figure 4:
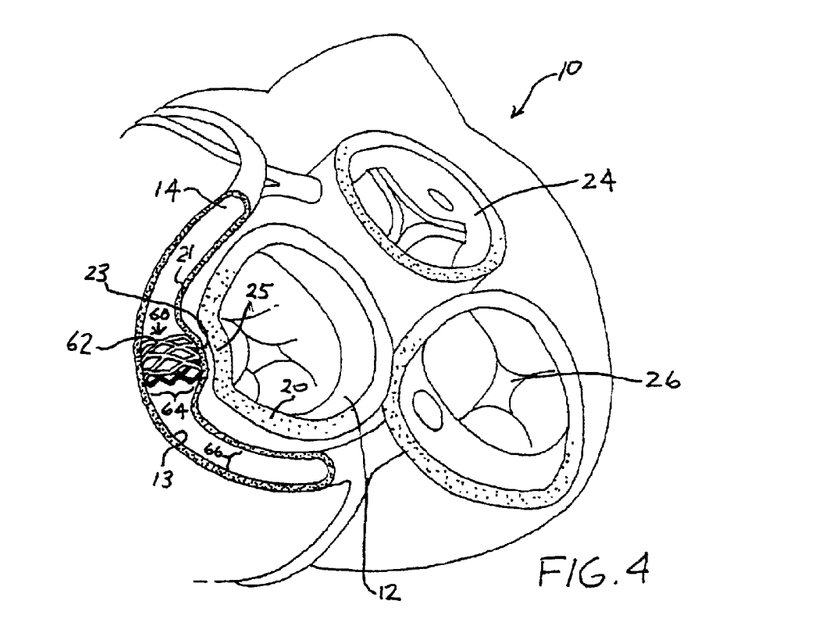
FIG. 4 is another superior view of a human heart similar to FIG. 1 illustrating a still further mitral valve device embodying the present invention.

Referring now to FIG. 4, it shows another mitral valve device 60 embodying the present invention implanted and deployed in the coronary sinus 14 of the heart 10. The device 60 takes the form of an expandable frame structure 62 which may be formed from Nitinol, for example. The device 60 may be first implanted in the coronary sinus 14 in a collapsed condition and then thereafter expanded to a deployed condition as illustrated. The device may be expanded by a balloon as known in the art, for example.

Alternatively, the device 60 may be self-expanding. More particularly, the frame structure may be formed from Nitinol or other similar titanium based elastic material known in the art and heat treated as is known in the art while the device is in its expanded deployment condition. This sets the device. However, the device may then be collapsed and advanced into the coronary sinus with a catheter. After reaching a desired location within the coronary sinus, the collapsed device may be released from the catheter. Upon being released, the device will spring or self-expand to its expanded set and deployed condition.

When deployed, the device 60 has a transverse cross-sectional dimension 64 greater than the unstressed cross-sectional dimension 66 of the coronary sinus 14. As a result, the device 60, when deployed, applies an applied force to a discrete portion 23 of the atrial wall 21 of the coronary sinus 14. This in turn applies the applied force to a discrete portion 25 of mitral valve annulus 20 to reshape the mitral valve annulus.

As will be particularly noted in FIG. 4, and also applicable to all of the embodiments of the present invention disclosed herein, the force applier has an axial length substantially less than one-half the circumference of the mitral valve annulus 20. This differs greatly from prior art devices which attempt to reshape the mitral valve annulus by circumscribing essentially the entire length of the mitral valve annulus that lies along the coronary sinus. While such devices may be effective, their generalized mitral valve annulus reshaping is in sharp contrast to the localized discrete reshaping of the mitral valve annulus provided by the devices and method of the present invention.

Figure 5:
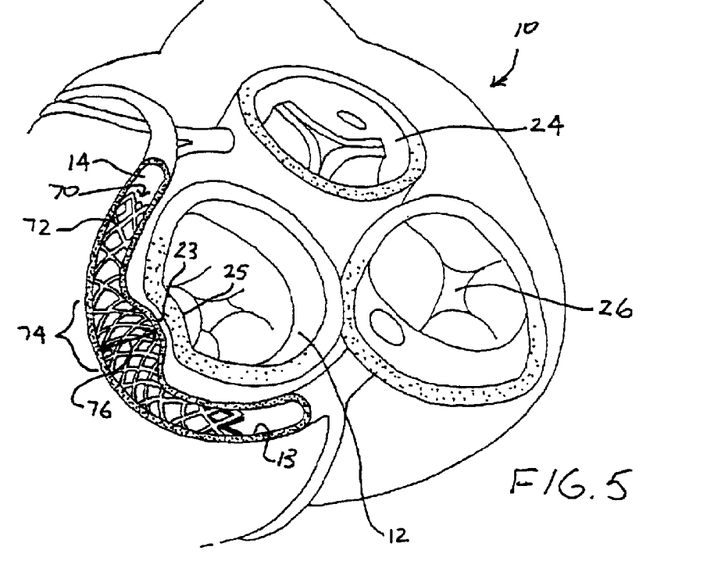
FIG. 5 is a further superior view of a human heart similar to that of FIG. 1 illustrating a still further mitral valve device embodying the present invention.

FIG. 5 shows another mitral valve device 70 embodying the present invention implanted in the coronary sinus 14 of the heart 10. The device 70 is an elongated frame structure 72. As will be noted in FIG. 5, the device 70 has a portion 74 of increased transverse dimension 76. The portion of increased transverse dimension 76 cause an applied force to be applied to a discrete portion 23 of the atrial wall of the coronary sinus 14. This in turn causes the applied force to be applied to a discrete portion 25 of the mitral valve annulus 20 to reshape the mitral valve annulus 20.

The frame structure 72 is preferably expandable from a collapsed condition permitting the device 70 to be implanted to an expanded deployed condition as illustrated to apply the applied force. The frame structure 72 is preferably self-expanding as previously described or may be expanded by other means such as by mechanical expansion or balloon expansion. For self-expansion, the frame structure is preferably formed from Nitinol or another titanium based elastic material. For mechanical or balloon expansion, the frame structure 72 may be formed from stainless steel, for example.

Figures 6, 7:
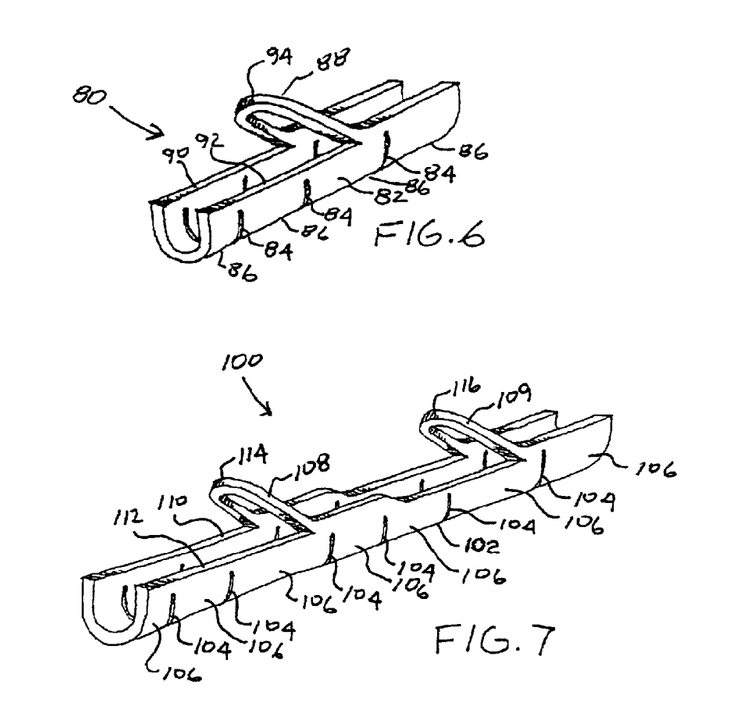
FIG. 6 is a perspective view of another mitral valve device embodying the present invention.
FIG. 7 is another perspective view of a further mitral valve device structured in accordance with the present invention.

FIG. 6 is a perspective view of another mitral valve device 80 embodying the present invention. The device has an elongated semi-tubular base 82 having cut-out portions 84 to allow bending of the base 82. Between the cut-out portions 84 are semi-cylindrical surfaces 86 arranged to continuously contact the pericardial wall of the coronary sinus when the device 80 is implanted in the coronary sinus to distribute the applied force.

The device 80 further includes a force applying member 88 which extends from opposed sidewalls 90 and 92 intermediate the ends of the base 82. The member 88 has an end 94 for engaging a discrete portion of the atrial wall of the coronary sinus to apply the applied force to a discrete portion of the mitral valve annulus to reshape the mitral valve annulus.

The device 80 may be formed by laser cutting a Nitinol tube or from another suitable material. The member 88 may be set in the illustrated position by heat treating but capable of resiliently bending in line with the sidewalls 90 and 92 for implanting and thereafter self expand to return to the deployed condition shown.

FIG. 7 is a perspective view of another mitral valve device 100 embodying the present invention which is similar to the device 80 of FIG. 6. The device 100 has an elongated semi-tubular base 102 having cut-out portions 104 to allow bending of the base 102. Between the cut-out portions 104 are semi-cylindrical surfaces 106 arranged to continuously contact the pericardial wall of the coronary sinus when the device 100 is implanted in the coronary sinus to distribute the applied force.

The device 100 further includes a pair of force applying members 108 and 109 which extend substantially parallel to each other from opposed sidewalls 110 and 112 intermediate the ends of the base 102. The members 108 and 109 each have an end 114 and 116 for engaging the atrial wall of the coronary sinus to apply the applied force to a plurality of discrete portions of the atrial wall of the coronary sinus to in turn apply the applied force to corresponding discrete portions of the mitral valve annulus to reshape the mitral valve annulus.

The device 100 may also be formed by laser cutting a Nitinol tube or from another suitable material. The members 108 and 109 may be set in the illustrated position by heat treating but capable of resiliently bending in line with the sidewalls 110 and 112 for implanting and to thereafter spring to the deployed condition as shown.

Figure 8:
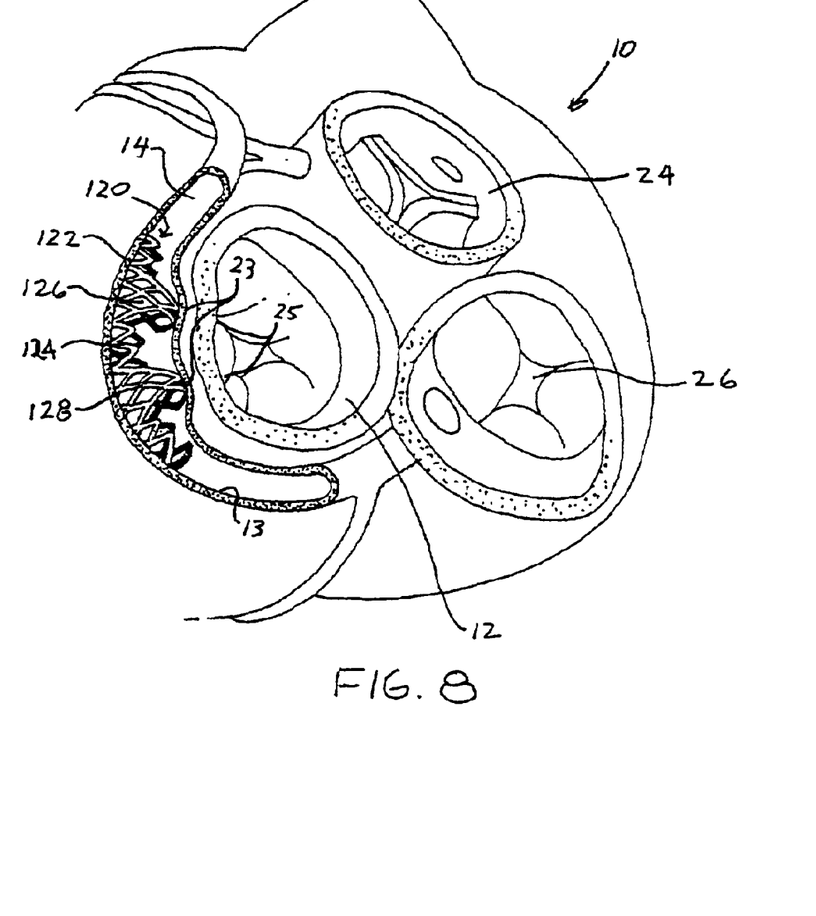
FIG. 8 is another superior view of a human heart similar to FIG. 1 illustrating a still another implanted mitral valve device embodying the present invention.

FIG. 8 shows still another mitral valve device 120 embodying the present invention implanted in the coronary sinus 14 of the heart 10. Like the device 100 of FIG. 7, it applies an applied force to a plurality of discrete portions 23 of the atrial wall of the coronary sinus 14 to in turn apply the force to a corresponding plurality of discrete portions 25 of the mitral valve annulus 20 to reshape the mitral valve annulus 20.

The device 120 takes the form of a frame structure 122 having an elongated base 124 that makes substantially continuous contact with the pericardial wall 13 of the coronary sinus 14.

The base 124 is semi-tubular. Extending from the base 124 are integral columnar structures 126 and 128. The columnar structures 126 and 128 form the force applier to apply the applied force to the plurality of discrete portions of the atrial wall of the coronary sinus.

The frame structure, like the other frame structures described herein, is expandable from a collapsed condition to permit implanting of the device to an expanded condition, once implanted, as shown. To that end, the frame structure 122 may be expanded by balloon expansion, mechanical expansion, or self expansion. When deployed as illustrated, the base 124 has a greater surface area than the columnar structures 126 and 128 to distribute the applied force along the pericardial wall 13 of the coronary sinus 14.

Figure 9:
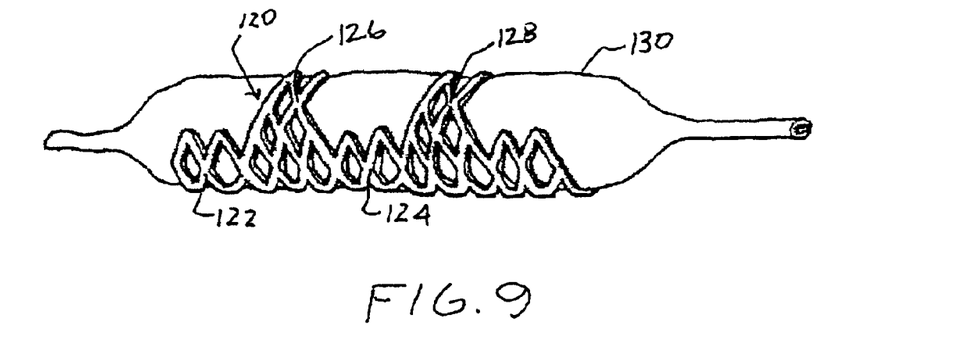
FIG. 9 is a side view of the device of FIG. 8 being expanded by a balloon into a deployed condition in accordance with the present invention.

FIG. 9 shows how the device 120 of FIG. 8 may be expanded with a balloon from its collapsed condition to its expanded condition. Here it may be seen that a balloon 130 is inserted into the device 120. Thereafter, the balloon 130 is inflated. As the balloon 130 inflates, it forces the frame structure 122 to expand to its expanded condition to form the deployed base 124 and then deployed columnar structures 126 and 128.

Figure 10:
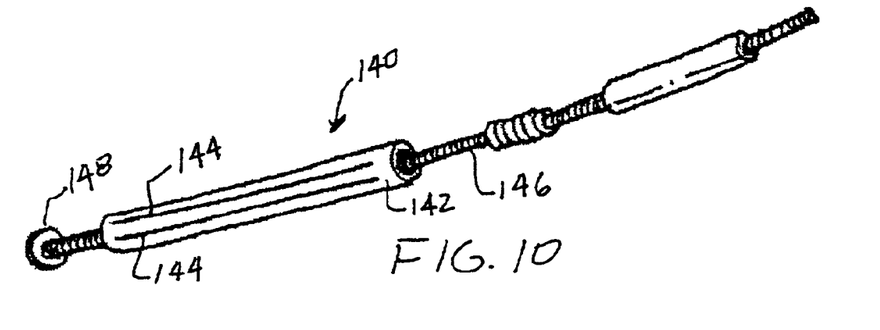
FIG. 10 is a perspective view of another mitral valve device shown in a collapsed condition in accordance with the present invention.
Figure 11:
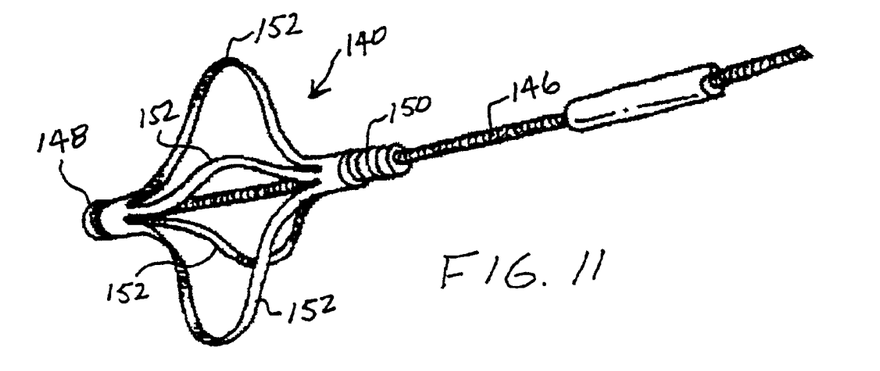
FIG. 11 is another perspective view of the device of FIG. 9 shown in an expanded deployed condition in accordance with the present invention.

FIGS. 10 and 11 show a still further device 140 embodying the present invention and which may be mechanically expanded to a deployed condition. As best seen in FIG. 10, the device 140, when in the collapsed condition, takes the form of a hollow cylinder 142 having slits 144 along its axial length. Extending through the hollow cylinder 142 is a pull wire 146. The pull wire terminates in an enlarged end 148.

As best seen in FIG. 11, when the collapsed device is positioned in the coronary sinus for deployment, the pull wire 136 is pulled proximally while the hollow cylinder 142 is held stationary against a grip spring 150. This causes the hollow cylinder to bend along the slits 144 like a toggle bolt to form a plurality of blades 152. The blades then form a force applier which apply a force to a discrete portion of the coronary sinus to reshape the mitral valve annulus.

Figure 12:
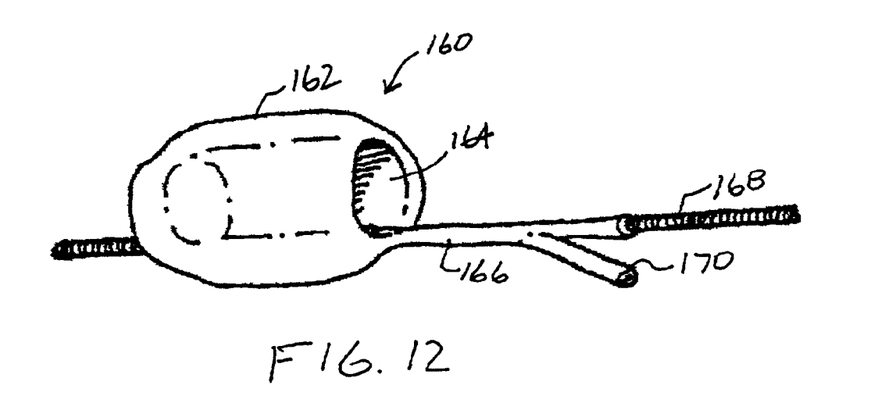
FIG. 12 is a perspective view of still another mitral valve device embodying the present invention.

FIG. 12 shows a still further device 160 embodying the present invention. Here the device is expandable as it takes the form of a balloon 162. The balloon, when inflated to a deployed condition has a hollow core 164 to permit blood flow through the coronary sinus. By being inflated, the device 160 is expanded for applying a force to a discrete portion of the coronary sinus to reshape the mitral valve annulus.

The balloon 162 is inflated by a balloon catheter 166 which carries the balloon 162. The balloon, when deflated, and the catheter 166 are guided into position within the coronary sinus by a guide wire 168 upon which the catheter 166 is mounted. When the balloon is positioned within the coronary sinus as desired, the balloon is inflated by the introduction of a fluid or gas into an inflation port 170 of the balloon catheter 166 for applying an applied force to a discrete portion of the mitral valve annulus. The device of FIG. 12 is particularly well suited for temporary use, for example, to measure the effectiveness of a device in various positions or of various sizes.

As may be seen from the foregoing, the present invention provides a mitral valve device and method for reshaping the mitral valve annulus to treat dilated cardiomyopathy. The devices apply an applied force to one or more desirable discrete portions of the atrial wall of the coronary sinus to reshape the adjacent mitral valve annulus in a localized, as opposed to a generalized, manner. Further, all of the embodiments disclosed herein avoid the crossover point of the circumflex artery and the coronary sinus.

While particular embodiments of the present invention have been shown and described, modifications may be made, and it is therefore intended in the appended claims to cover all such changes and modifications which fall within the true spirit and scope of the invention.

What is claimed:

1. A mitral valve therapy device configured to be placed in the coronary sinus of a heart adjacent to the mitral valve annulus, the device comprising a force applier that applies an applied force to a discrete portion of the atrial wall of the coronary sinus adjacent to the mitral valve annulus to concentrate the applied force on a discrete portion of the mitral valve annulus.

2. The device of claim 1 wherein the coronary sinus has an unstressed cross-sectional dimension and wherein the force applier has a cross-sectional dimension greater than the unstressed cross-sectional dimension of the coronary sinus to change the shape of the mitral valve annulus.

3. The device of claim 1 wherein the force applier applies the applied force to a plurality of discrete portions of the atrial wall of the coronary sinus.

4. A mitral valve therapy device configured to be placed in the coronary sinus of a heart adjacent to the mitral valve annulus, the device comprising a force applier that applies an applied force to a discrete portion of the atrial wall of the coronary sinus adjacent to the mitral valve annulus to concentrate the applied force on a discrete portion of the mitral valve annulus, wherein the mitral valve annulus has a circumference, wherein the coronary sinus has a cross sectional diameter, and wherein the force applier has an axial length substantially less than half the circumference of the mitral valve annulus and a deployed transverse dimension greater than the diameter of the coronary sinus.

5. The device of claim 4 wherein the device comprises an expandable structure that expands from a collapsed condition to an expanded condition defining the deployed transverse dimension.

6. The device of claim 5 wherein the expandable structure is self-expandable.

7. The device of claim 5 wherein the expandable structure is mechanically expandable.

8. The device of claim 7 wherein the expandable structure is pull wire expandable.

9. The device of claim 5 wherein the device is cylindrical in configuration.

10. The device of claim 9 wherein the device is a frame structure.

11. The device of claim 10 wherein the frame structure is balloon expandable.

12. A mitral valve therapy device configured to be placed in the coronary sinus of a heart adjacent to the mitral valve annulus, the device comprising a force applier that applies an applied force to a discrete portion of the atrial wall of the coronary sinus adjacent to the mitral valve annulus to concentrate the applied force on a discrete portion of the mitral valve annulus, the device further including a force distributor that distributes the applied force along a pericardial wall of the coronary sinus.

13. The device of claim 12 wherein the force applier applies the applied force to a plurality of discrete portions of the atrial wall of the coronary sinus.

14. The device of claim 12 wherein the force distributor has a surface area, wherein the force applier has a surface area defining the discrete portion, and wherein the surface area of the force distributor is greater than the surface area of the force applier.

15. A mitral valve therapy device configured to be placed in the coronary sinus of a heart adjacent to the mitral valve annulus, the device comprising a force applier that applies an applied force to a discrete portion of the atrial wall of the coronary sinus adjacent to the mitral valve annulus to concentrate the applied force on a discrete portion of the mitral valve annulus, wherein the force applier is a balloon.

16. A mitral valve therapy device configured to be placed in the coronary sinus of a heart adjacent to the mitral valve annulus, the device comprising:

a force distributor that distributes an applied force along a pericardial wall of the coronary sinus;

a force applier that applies the applied force to at least one discrete portion of a wall of the coronary sinus adjacent to the mitral valve annulus to concentrate the applied force on at least one discrete portion of the mitral valve annulus.

17. The device of claim 16 wherein the mitral valve annulus has a circumference and wherein the force applier has a length substantially less than one half the mitral valve annulus circumference.

18. The device of claim 16 wherein the force applier applies the applied force to a plurality of discrete portions of the wall of the coronary sinus adjacent to the mitral valve annulus.

19. The device of claim 16 wherein the force distributor comprises an elongated first member configured to substantially continuously contact the pericardial wall of the coronary sinus and wherein the force applier comprises a second member extending from the first member at an angle, the second member having an end that applies the applied force.

20. The device of claim 19 wherein the second member is resiliently connected to the first member.

21. The device of claim 19 wherein the first and second members are integrally formed from a same elongated member.

22. The device of claim 21 wherein the same elongated member is formed from a resilient material.

23. The device of claim 19 wherein the first member has opposed ends and wherein the second member extends from the first member intermediate the opposed ends of the first member.

24. The device of claim 23 wherein the force applier further includes at least one additional member extending from the first member intermediate the opposed ends of the first member.

25. The device of claim 24 wherein the at least one additional member extends from the first member substantially parallel to the second member.

26. The device of claim 24 wherein the first and second members form an integral structure.

27. The device of claim 24 wherein the plurality of columnar frame structures are expandable from a collapsed condition to an expanded columnar condition.

28. The device of claim 27 wherein the plurality of columnar frame structures are self-expandable.

29. The device of claim 27 wherein the plurality of columnar frame structures are balloon expandable.

30. The device of claim 16 wherein the force distributor is an elongated frame structure and wherein the force applier comprises at least one columnar frame structure extending from the elongated frame structure.

31. The device of claim 30 wherein the at least one columnar frame structure is expandable from a collapsed condition to an expanded columnar condition.

32. The device of claim 31 wherein the at least one columnar frame structure is self-expandable.

33. The device of claim 31 wherein the at least one columnar frame structure is balloon expandable.

34. The device of claim 30 wherein the elongated frame structure is expandable from a collapsed condition to an expanded condition.

35. The device of claim 34 wherein the elongated frame structure is self-expandable.

36. The device of claim 34 wherein the elongated frame structure is balloon expandable.

37. The device of claim 30 wherein the force applier comprises a plurality of columnar frame structures.

38. The device of claim 16 wherein the device is an elongated frame structure, the elongated frame structure having a portion of increased transverse dimension to form the force applier.

39. The device of claim 38 wherein the elongated frame structure is expandable in transverse dimension.

40. The device of claim 39 wherein the elongated frame structure is self-expandable.

41. The device of claim 39 wherein the elongated frame structure is balloon expandable.

42. The device of claim 16 wherein the device is an elongated member having outwardly curved end portions that engage the pericardial wall of the coronary sinus to form the force distributor and an inwardly curved portion between the outwardly curved end portions to form the force applier.

43. A method of treating dilated cardiomyopathy of a heart including the step of applying a force to a discrete localized portion of an atrial wall of a coronary sinus to concentrate the force on a corresponding localized portion of a mitral valve annulus to change the shape of the mitral valve annulus.

44. A method of treating dilated cardiomyopathy of a heart including the step of applying a force to a discrete localized portion of an atrial wall of a coronary sinus to concentrate the force on a corresponding localized portion of a mitral valve annulus to change the shape of the mitral valve annulus, wherein the applying step includes inflating a balloon within the coronary sinus.

45. The method of claim 43 wherein the applying step includes the step of implanting a force applying device in the coronary sinus, the device applying the force to the discrete localized portion of the coronary sinus.

46. A method of treating dilated cardiomyopathy of a heart including the step of applying a force to a discrete localized portion of an atrial wall of a coronary sinus to concentrate the force on a corresponding localized portion of a mitral valve annulus to change the shape of the mitral valve annulus, wherein the applying step includes the step of implanting a force applying device in the coronary sinus, the device applying the force to the discrete localized portion of the coronary sinus, wherein the device is expandable from a collapsed condition to a deployed condition, wherein the implanting step is carried out while the device is in the collapsed condition, and wherein the applying step further includes the step of expanding the device to the deployed condition after the device is implanted.

47. The method of claim 46 wherein the expanding step includes expanding the device with a balloon.

48. The method of claim 46 wherein the expanding step includes mechanically expanding the device.

49. A method of treating dilated cardiomyopathy of a heart including the step of applying a force to a discrete localized portion of an atrial wall of a coronary sinus to concentrate the force on a corresponding localized portion of a mitral valve annulus to change the shape of the mitral valve annulus and distributing the applied force along a pericardial wall of the coronary sinus.

50. The method of claim 49 wherein the applying step includes the step of applying the force to a plurality of discrete localized portions of the atrial wall of the coronary sinus while distributing the applied force along the pericardial wall of the coronary sinus.

51. The method of claim 50 wherein the applying step includes the step of implanting a force applying device in the coronary sinus, the device applying the force to the plurality of discrete localized portions of the coronary sinus.

52. The method of claim 51 wherein the device is expandable from a collapsed condition to a deployed condition, wherein the implanting step is carried out while the device is in the collapsed condition, and wherein the applying step further includes the step of expanding the device to the deployed condition after the device is implanted.

53. The method of claim 52 wherein the expanding step includes expanding the device with a balloon.

54. The method of claim 52 wherein the expanding step includes mechanically expanding the device.

55. A mitral valve therapy device configured to be placed in the coronary sinus of a heart adjacent to the mitral valve annulus, the device comprising force applying means for applying an applied force to a discrete portion of the atrial wall of the coronary sinus adjacent to the mitral valve annulus for concentrating the applied force on a discrete portion of the mitral valve annulus.

56. The device of claim 55 wherein the coronary sinus has an unstressed cross-sectional dimension and wherein the force applying means has a cross-sectional dimension greater than the unstressed cross-sectional dimension of the coronary sinus for changing the shape of the mitral valve annulus.

57. The device of claim 55 wherein the force applying means includes means for applying the applied force to a plurality of discrete portions of the atrial wall of the coronary sinus.

58. A mitral valve therapy device configured to be placed in the coronary sinus of a heart adjacent to the mitral valve annulus, the device comprising force applying means for applying an applied force to a discrete portion of the atrial wall of the coronary sinus adjacent to the mitral valve annulus for concentrating the applied force on a discrete portion of the mitral valve annulus, wherein the force applying means is a balloon.

59. A mitral valve therapy device configured to be placed in the coronary sinus of a heart adjacent to the mitral valve annulus, the device comprising force applying means for applying an applied force to a discrete portion of the atrial wall of the coronary sinus adjacent to the mitral valve annulus for concentrating the applied force on a discrete portion of the mitral valve annulus, wherein the mitral valve annulus has a circumference, wherein the coronary sinus has a cross sectional diameter, and wherein the force applying means has an axial length substantially less than half the circumference of the mitral valve annulus and a deployed transverse dimension greater than the diameter of the coronary sinus.

60. A mitral valve therapy device configured to be placed in the coronary sinus of a heart adjacent to the mitral valve annulus, the device comprising force applying means for applying an applied force to a discrete portion of the atrial wall of the coronary sinus adjacent to the mitral valve annulus for concentrating the applied force on a discrete portion of the mitral valve annulus, wherein the device comprises expandable structure means for expanding from a collapsed condition to an expanded deployed condition.

61. The device of claim 60 wherein the expandable structure means is mechanically expandable.

62. The device of claim 60 wherein the expandable structure means is balloon expandable.

63. A mitral valve therapy device configured to be placed in the coronary sinus of a heart adjacent to the mitral valve annulus, the device comprising force applying means for applying an applied force to a discrete portion of the atrial wall of the coronary sinus adjacent to the mitral valve annulus for concentrating the applied force on a discrete portion of the mitral valve annulus, the device further including force distributing means for distributing the applied force along a pericardial wall of the coronary sinus.

64. The device of claim 63 wherein the force distributing means has a surface area, wherein the force applying means has a surface area defining the at least one discrete portion, and wherein the surface area of the force distributing means is greater than the surface area of the force applying means.

65. A mitral valve therapy device configured to be placed in the coronary sinus of a heart adjacent to the mitral valve annulus, the device comprising:
   force distributing means for distributing an applied force along a pericardial wall of the coronary sinus; and
   force applying means for applying the applied force to at least one discrete portion of a wall of the coronary sinus adjacent to the mitral valve annulus to concentrate the applied force on at least one discrete portion of the mitral valve annulus.

* * * * *